US009415171B2

(12) United States Patent
Peterson

(10) Patent No.: US 9,415,171 B2
(45) Date of Patent: Aug. 16, 2016

(54) NEEDLE BENDING APPARATUS AND METHODS

(71) Applicant: Innovative Products & Equipment Inc., Tyngsboro, MA (US)

(72) Inventor: Eric Peterson, Tyngsboro, MA (US)

(73) Assignee: Innovative Products & Equipment Inc., Tyngsboro, MA (US)

( * ) Notice: Subject to any disclaimer, the term of this patent is extended or adjusted under 35 U.S.C. 154(b) by 315 days.

(21) Appl. No.: 13/741,763

(22) Filed: Jan. 15, 2013

(65) Prior Publication Data
US 2014/0196517 A1    Jul. 17, 2014

(51) Int. Cl.
*B21D 7/024* (2006.01)
*B21F 45/00* (2006.01)
*A61M 5/32* (2006.01)

(52) U.S. Cl.
CPC .............. *A61M 5/32* (2013.01); *A61M 5/329* (2013.01); *B21D 7/024* (2013.01); *B21F 45/008* (2013.01)

(58) Field of Classification Search
CPC ............ B21D 7/02; B21D 7/024; B21F 1/00; B21F 1/006; B21F 45/008
USPC ................... 72/296, 298, 306, 307
See application file for complete search history.

(56) References Cited

U.S. PATENT DOCUMENTS

| 6,434,995 B1 * | 8/2002 | Kataoka ................ B21D 7/024 72/149 |
| 2010/0043515 A1 * | 2/2010 | Bourset ........................... 72/224 |
| 2010/0275668 A1 * | 11/2010 | Riemeier et al. ................ 72/293 |

* cited by examiner

*Primary Examiner* — Debra Sullivan
(74) *Attorney, Agent, or Firm* — McCarter & English, LLP; Jonathan M. Sparks; Heath T. Misley

(57) ABSTRACT

An apparatus for bending a hypodermic needle includes a bending die, a needle gripper configured to grasp the hypodermic needle, a servo-actuated slide operatively coupled to the needle gripper, and a servo- or pneumatically-actuated bending pin. The servo-actuated slide is configured to translate the needle gripper along a linear path adjacent to the bending die for positioning the hypodermic needle at a predetermined bending position with respect to the bending die. The bending pin is rotatable about a bending axis passing through the linear path. The bending pin is configured to press a portion of the hypodermic needle against the bending die as the bending pin rotates to form a bend in the hypodermic needle.

14 Claims, 13 Drawing Sheets

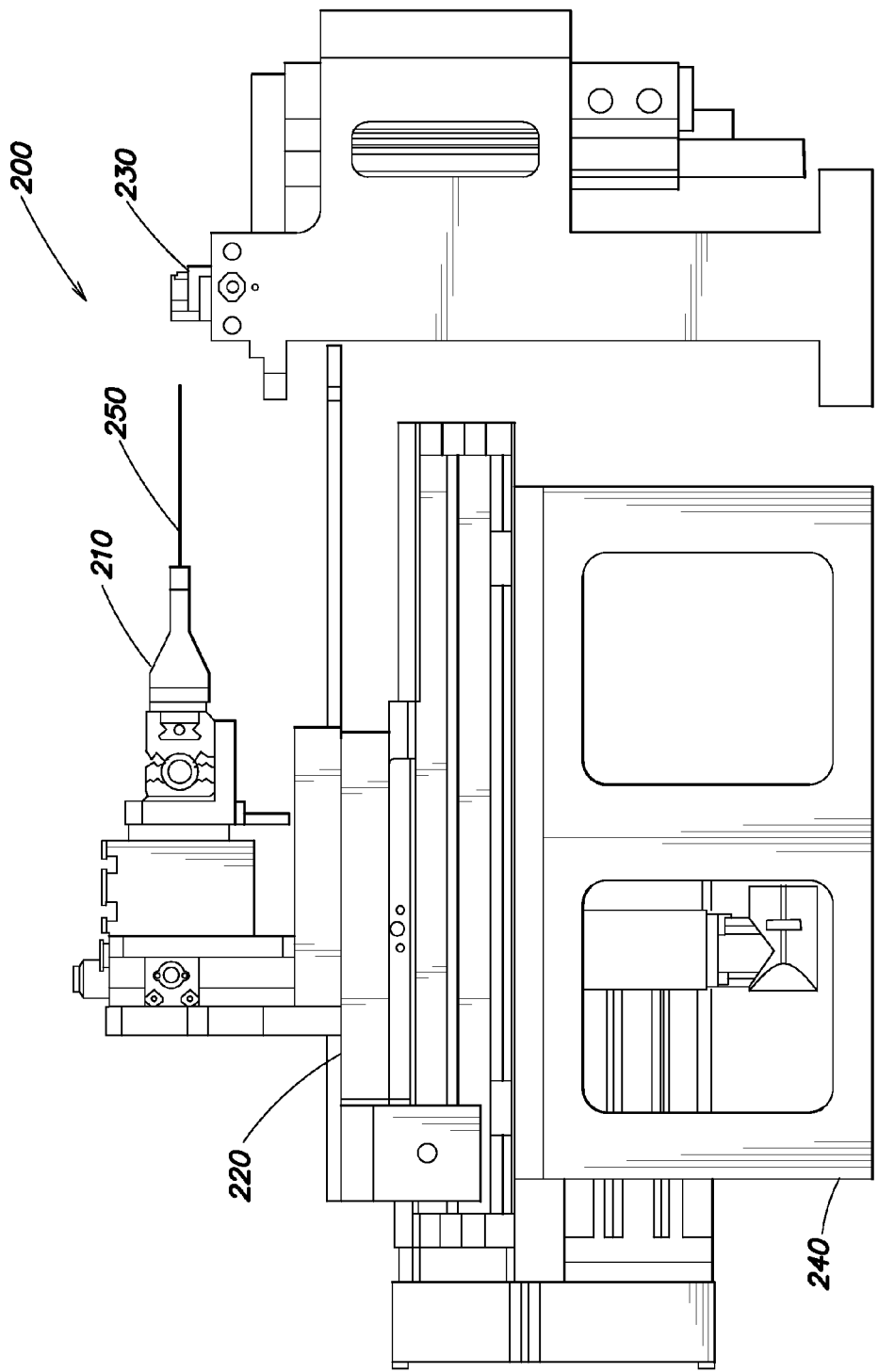

NEEDLE BENDING APPARATUS AND METHODS

BACKGROUND

1. Field of Invention

Embodiments of the invention relate generally to needle bending, and more particularly to apparatus and methods of forming one or more bends in a hypodermic needle.

2. Description of Related Art

Hypodermic needles having one or more strategically-placed bends have advantages over straight needles in many medical applications. For example, dialysis patents undergo many hours of treatment each week in which a needle is inserted into one arm and taped down to the skin to prevent dislodgement. In this arrangement, a straight needle can press against the tissue beneath the skin in a manner that may be uncomfortable to the patent. To improve comfort, the needle may be bent so as to lie against the arm after it is inserted. The location and angle of the bend may vary according to the application and the size of the needle.

One conventional technique for bending hypodermic needles includes manually bending the needle using a forming tool. However, this technique is imprecise, slow and inefficient, and also introduces the possibility of inadvertently crushing the lumen or otherwise damaging the needle as a result of excessive force or improper use of the tool. It can also be difficult, if not impossible, to form multiple bends in the needle using the tool, especially where the bends are to be formed at different angles or in different directions away from the length-wise axis of the unbent needle. Furthermore, manual needle bending techniques are not suited for mass production of bent needles. Other semi-automated bending techniques have been developed but still do not provide the ability to precisely form one or more bends in a repeatable and efficient manner.

SUMMARY

According to one embodiment, an apparatus for bending a hypodermic needle includes a bending die, a needle gripper configured to grasp the hypodermic needle, a servo-actuated slide operatively coupled to the needle gripper, and a servo- or pneumatic-actuated bending pin. The servo-actuated slide is configured to translate the needle gripper along a linear path adjacent to the bending die for positioning the hypodermic needle at a predetermined bending position with respect to the bending die. The bending pin is rotatable about a bending axis passing through the linear path, and is configured to press a portion of the hypodermic needle against the bending die as the bending pin rotates to form a bend in the hypodermic needle.

In another embodiment, the needle gripper may include a servo-actuated rotating device configured to rotate the hypodermic needle, via the needle gripper, with respect to the bending die. In yet another embodiment, the hypodermic needle may have a bevel at a first end thereof and a second end opposite the first end. The apparatus may further include a machine vision device configured to determine whether the bevel is correctly oriented with respect to the needle gripper, determine a first needle position along the linear path corresponding to the first end of the hypodermic needle, and/or determine a second needle position along the linear path corresponding to the second end of the hypodermic needle.

In another embodiment, the apparatus may include a pick-and-place device configured to place the hypodermic needle into the needle gripper. In yet another embodiment, the apparatus may include a bevel orienting device configured to orient the bevel with respect to the needle gripper. In yet another embodiment, the apparatus may include a hopper configured to contain the hypodermic needle, and a needle singulator configured to move the hypodermic needle between the hopper and the bevel orienting device.

In another embodiment, the apparatus may include a programmable controller operatively coupled to the needle gripper, the servo-actuated slide, the bending pin, the machine vision device, the pick-and-place device and/or the needle singulator. The controller may be programmatically configured to cause the servo-actuated slide to translate the needle gripper along the linear path to position the hypodermic needle at the predetermined bending position based on the first needle position and/or the second needle position, and cause the servo- or pneumatic-actuated bending pin to press the portion of the hypodermic needle against the bending die for forming a bend in the hypodermic needle. In yet another embodiment, the controller may be programmatically configured to cause the needle singulator to move the hypodermic needle between the hopper and the bevel orienting device, cause the pick-and-place device to place the hypodermic needle into the needle gripper, cause the needle gripper to grasp the hypodermic needle, and/or cause the servo-actuated rotating device to rotate the hypodermic needle, via the needle gripper, with respect to the bending die to adjust for movement of the hypodermic needle along an axial length of the bending pin as the bending pin rotates or to create a three-dimensional bend in the hypodermic needle.

In another embodiment, the predetermined bending position may be a first predetermined bending position, the portion of the hypodermic needle may be a first portion of the hypodermic needle, and the bend in the hypodermic needle may be a first bend in the hypodermic needle. The controller may be further programmatically configured to cause the servo-actuated slide to translate the needle gripper along the linear path to position the hypodermic needle at a second predetermined bending position, and cause the servo- or pneumatic-actuated bending pin to press a second portion of the hypodermic needle against the bending die to form a second bend in the hypodermic needle.

In another embodiment, the controller may be further programmatically configured to cause the needle gripper to rotate through a predetermined angle prior to or while causing the servo- or pneumatic-actuated bending pin to press the second portion of the hypodermic needle against the bending die.

In another embodiment, the apparatus may include a user interface operatively coupled to the controller and configured to receive commands from a user. The commands may represent a position along a length of the hypodermic needle, a bending direction and a bending angle for each bend to be formed in the hypodermic needle. The controller may be further configured to receive the commands and to cause the apparatus to form each bend in the hypodermic needle according to the commands.

In another embodiment, the apparatus may include a needle restraining member coupled to one end of the bending pin. The needle restraining member may be configured to limit movement of the hypodermic needle along an axial length of the bending pin as the bending pin rotates. In yet another embodiment, the bending pin may be further configured to extend and retract between two positions along an axis passing through the bending pin.

According to one embodiment, a method of bending a hypodermic needle includes grasping the hypodermic needle using a rotatable needle gripper, translating the rotatable needle gripper along a linear path to position the hypodermic needle at a predetermined bending position with respect to a bending die using a servo-actuated slide operatively coupled to the needle gripper, and pressing a portion of the hypodermic needle against the bending die using a servo- or pneumatic-actuated rotating bending pin to form a bend in the hypodermic needle. The bend is formed by rotating the bending pin about a bending axis passing through the linear path.

In another embodiment, the hypodermic needle may have a bevel at a first end thereof and a second end opposite the first end. The method may include determining whether the bevel is correctly oriented with respect to the rotatable needle gripper using a machine vision device, determining a first needle position along the linear path corresponding to the first end of the hypodermic needle using the machine vision device, and/or determining a second needle position along the linear path corresponding to the second end of the hypodermic needle using the machine vision device. In yet another embodiment, the step of translating the rotatable needle gripper along a linear path to position the hypodermic needle at the predetermined bending position may be performed based on the first needle position and/or the second needle position.

In another embodiment, the predetermined bending position may be a first predetermined bending position, the portion of the hypodermic needle may be a first portion of the hypodermic needle, and the bend in the hypodermic needle may be a first bend in the hypodermic needle. The method may include translating the rotatable needle gripper along the linear path to position the hypodermic needle at a second predetermined bending position using the servo-actuated slide. In yet another embodiment, the method may include rotating the rotatable needle gripper through a predetermined angle about the linear path using a servo-actuated rotating device prior to pressing the second portion of the hypodermic needle against the bending die. In yet another embodiment, the method may include pressing a second portion of the hypodermic needle against the bending die to form a second bend in the hypodermic needle using the servo- or pneumatic-actuated bending pin such that the hypodermic needle is bent in three dimensions.

According to one embodiment, an apparatus for bending a hypodermic needle includes a needle gripper configured to grasp the hypodermic needle, a bending means for forming a bend in the hypodermic needle, and a slide operatively coupled to the needle gripper. The slide is configured to translate the needle gripper along a linear path adjacent to the bending means to position the hypodermic needle at a predetermined bending position with respect to the bending means. In another embodiment, the apparatus may include a controlling means for causing the bending means to form the bend in the hypodermic needle.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2B is a side elevation view of the needle bending apparatus of FIG. 2A;

DETAILED DESCRIPTION

Embodiments include apparatus and methods of producing bent needles from straight needles. In one embodiment, an apparatus is configured to form one or more bends in a hypodermic needle in various directions and at various angles. The apparatus is programmable such that it can form different, user-selectable bends of any desired radius and/or angle with little or no tooling changes to the apparatus. The programmability of the apparatus further permits the apparatus to be easily adapted to any variations in the needle lots, for example, by operator-adjusting various bending parameters via a user interface.

Straight needles may, for example, be supplied in bulk with the beveled ends oriented in the same direction. Each needle is individually loaded into a needle gripper and advanced to a needle bender using a servo-actuated slide mechanism. In some embodiments, the apparatus includes a machine vision system with one or more cameras for identifying the position of at least one end of the needle and/or verifying the orientation of the needle. The position of the needle end can be used to accurately position the needle in the needle bender. The needle bender includes a servo- or pneumatic-actuated bending pin that rotates to press the needle against a bending die to form a bend. Each bend can be formed at a specific location on the needle and at a specific angle. In some embodiments, bends can be formed in two or three dimensions by rotating the needle with respect to the needle bender. The apparatus is programmable such that any needle shape can be formed using a combination of bends and linear advances of the needle. Once the needle is bent to the desired shape it may be deposited, for example, onto a conveyor for transport to an operator or receptacle.

Figure 1:
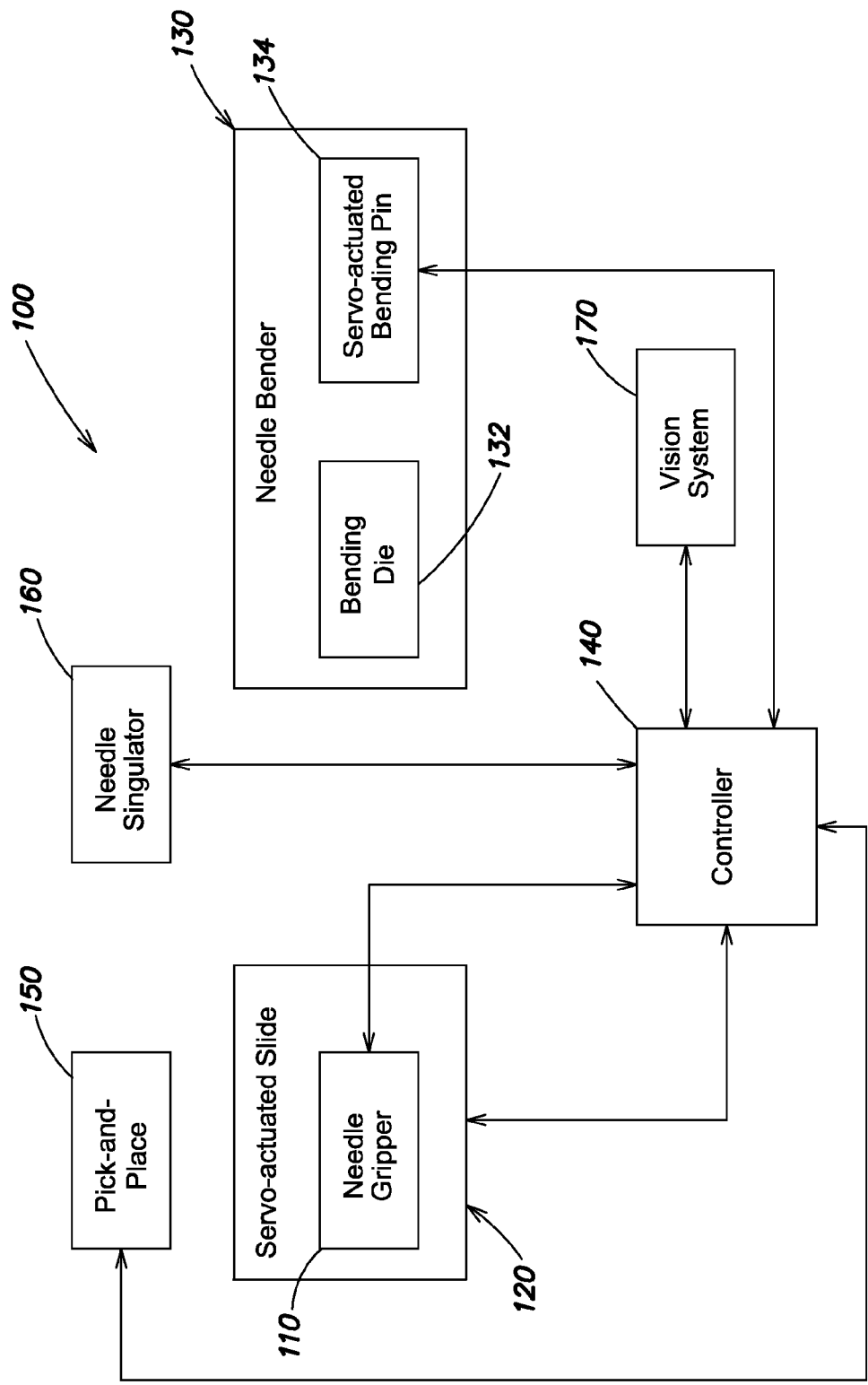
FIG. 1 is a block diagram of a needle bending apparatus in accordance with one embodiment.

FIG. 1 is a block diagram of a needle bending apparatus 100, according to one embodiment. The apparatus 100 includes a needle gripper 110, a servo-actuated slide 120, a needle bender 130 and a programmable controller 140. The needle bender 130 includes a bending die 132 and a servo-actuated rotating bending pin 134. In some embodiments, the bending pin 134 may be pneumatically actuated. The needle gripper 110 is mounted to the servo-actuated slide 120, which in turn may be mounted to a frame, table or other support structure (not shown). Furthermore, the needle bender 130 may also be mounted to the frame or table, or to a different structure. In some embodiments, the apparatus 100 further includes a pick-and-place device 150, a needle singulator 160 and/or a machine vision system 170.

The controller 140 is operatively connected to the needle gripper 110, the servo-actuated slide 120, the needle bender 130, the pick-and-place device 150, the needle singulator 160 and/or the machine vision system 170. The controller 140 may include, for example, a programmable logic controller such as an Allen-Bradley PLC-5 Control System, 1756 ControlLogix Control System, SLC 500 Control System, or MicroLogix Control System, all sold by Rockwell Automation of Milwaukee, Wis., or other similar programmable controller device. The control system may further include a human-machine interface (HMI) for enabling an operator to control and monitor the operation of the apparatus 200. The machine vision system 170 may include, for example, an InSight® Vision System sold by Cognex Corporation of Natick, Mass.

In one embodiment, the apparatus 100 generally functions as follows: the needle singulator 160 removes a single needle from a bulk hopper or other supply source. An optional bevel orienting device associated with the needle singulator 160 may roll the needle until the bevel is in a desired orientation. The pick-and-place device 150 transfers the needle to the needle gripper 110. The needle gripper 110 grasps a portion of the initially straight needle, with one end of the needle (e.g., the beveled end) extending out of the needle gripper 110. The servo-actuated slide 120, under control of the controller 140, moves the needle gripper 110 toward the needle bender 130, e.g., along a linear path adjacent to the bending die 132.

The machine vision system 170 locates one or both ends of the needle as it is being grasped by the needle gripper 110, and the location can be used by the controller 140 for precisely positioning the needle with respect to the needle bender 130. In one embodiment, the needle gripper 110 can rotate the needle, which allows the needle to be oriented rotationally with respect to the needle bender 130 for forming bends in three dimensions. In another embodiment, the machine vision system 170 can be used to orient the bevel of the needle with respect to the needle bender 130, although in some embodiments the bevel can be oriented using a mechanical bevel orienting mechanism prior to transferring the needle to the needle gripper 110.

As discussed above, the needle gripper 130 and needle can be moved along the linear path by the servo-actuated slide 120 until the needle is positioned at a predetermined bending position with respect to the bending die 132. The needle may be positioned, for example, based on the location of one or both ends of the needle, as determined by the machine vision system 170, relative to the bending die 132. The bending die 132 is configured such that a bend can be formed in the needle by pressing the needle against the bending die 132 using the servo- (or pneumatically-) actuated bending pin 134, which rotates about the bending die 132 in a clockwise or counterclockwise direction. Thus the bend is formed at a location along the length of the needle corresponding to the predetermined bending position. The angle and direction of the bend can be variably formed depending on how far and in which direction the servo- (or pneumatically-) actuated bending pin 134 rotates. After the bend is formed, the bending pin 134 either rotates away from the needle or retracts so as not to obstruct further advancement of the needle along the linear path. One or more additional bends may be formed in the needle by advancing the needle gripper 110, and the needle, toward the needle bender 130 to different pre-determined bending positions after each bend is formed, and then pressing the needle against the bending die 132, again by rotating the servo- (or pneumatically-) actuated bending pin 134. In embodiments where the needle gripper 110 is rotatable, the needle can be rotated between bends to form bends in different directions (i.e., in three dimensions).

Figure 2A:
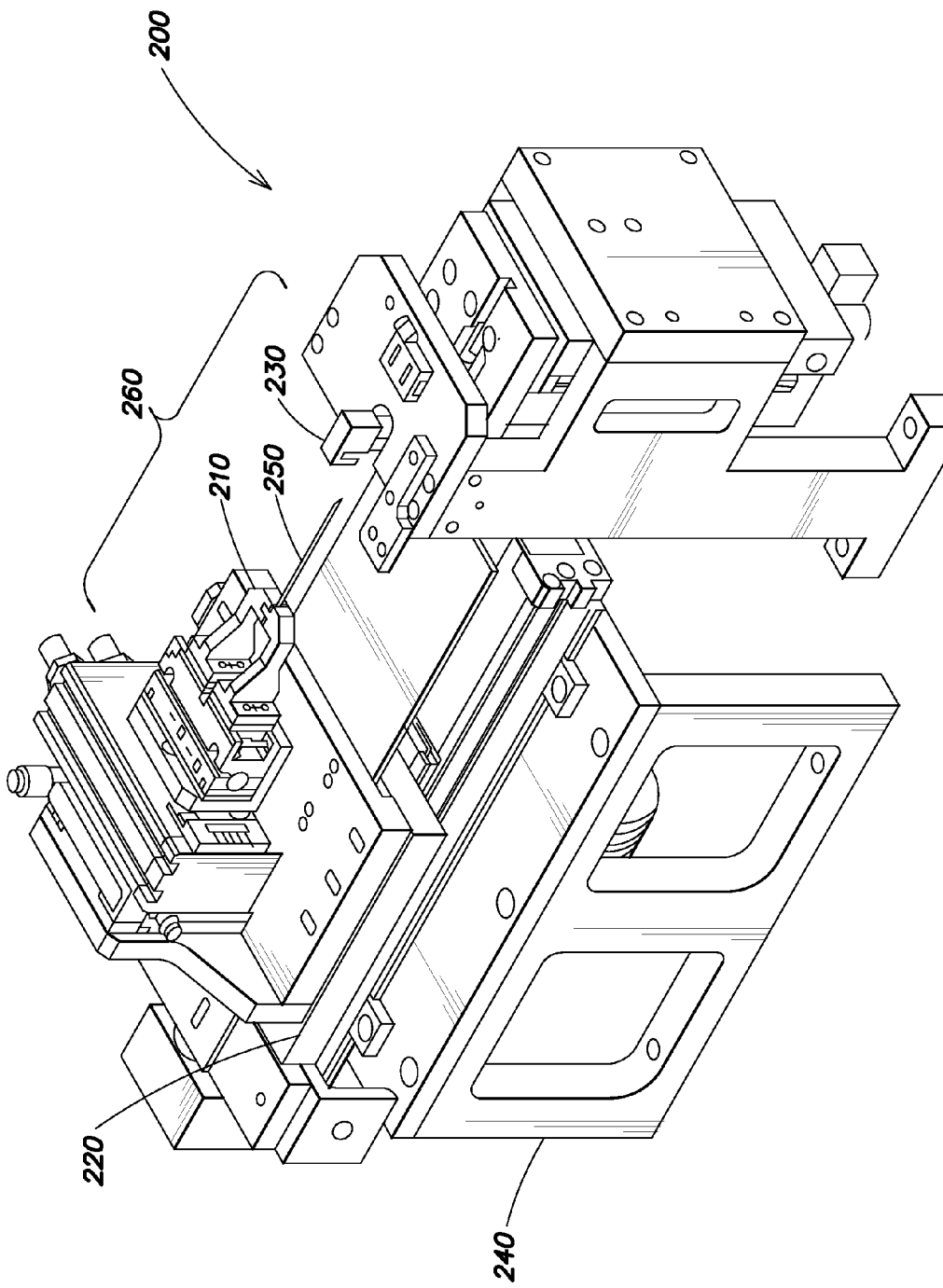
FIG. 2A is a perspective view of a needle bending apparatus in accordance with one embodiment.

FIG. 2A is a perspective view of a needle bending apparatus 200, according to one embodiment. The apparatus 200 includes a needle gripper 210, a servo-actuated slide 220, a servo-actuated needle bender 230, and a frame 240. The apparatus 200 may also include a controller, a needle singulator and a pick-and-place device (not shown). The apparatus 200 may, in some embodiments, function substantially as described with respect to FIG. 1. For illustrative purposes only, a needle 250 (e.g., a hypodermic needle) is depicted extending out from the needle gripper 210 and toward the needle bender 230, although it will be understood that the needle 250 is not necessarily part of the apparatus 200. Further, the needle 250 may be of varying lengths and may be positioned and/or oriented in various configurations with respect to the apparatus 200. The combination of the needle gripper 210, the servo-actuated slide 220 and the servo-actuated needle bender 230 is also referred to herein as a needle bending module 260.

The needle gripper 210, in one embodiment, is configured to grasp the needle 250 such that at least a portion of the needle 250 extends away from the needle gripper 210. The needle gripper 210 may, for example, include a pair of clamps or grips that can be moved toward or away from each other for grasping and releasing the needle 250. The needle gripper 210 may be electrically, pneumatically and/or hydraulically operated by actuators (not shown), which may be controlled by the controller.

In one embodiment, the apparatus 200 includes between one and six needle bending modules 260 attached to the frame 240 (only one is shown in FIG. 2A), although it will be understood that in some embodiments the apparatus 200 can be configured to include any number of needle bending modules 260. Each needle bending module 260 can operate independently of other needle bending modules and share power and the control system of the apparatus 200.

In some embodiments, the apparatus 200 may further include a bulk needle feeder for feeding needles to the needle gripper 210, a machine vision system for identifying the ends of needles held by the needle gripper 210 (e.g., to position the needle 250), an unloading device for removing bent needles from the apparatus 200, a conveyor for depositing bent needles into a bin or hopper, pneumatic valves for operating certain components of the apparatus 200, and/or a remote input/output module for interfacing one or more of the above elements with the controller.

Figure 2C:
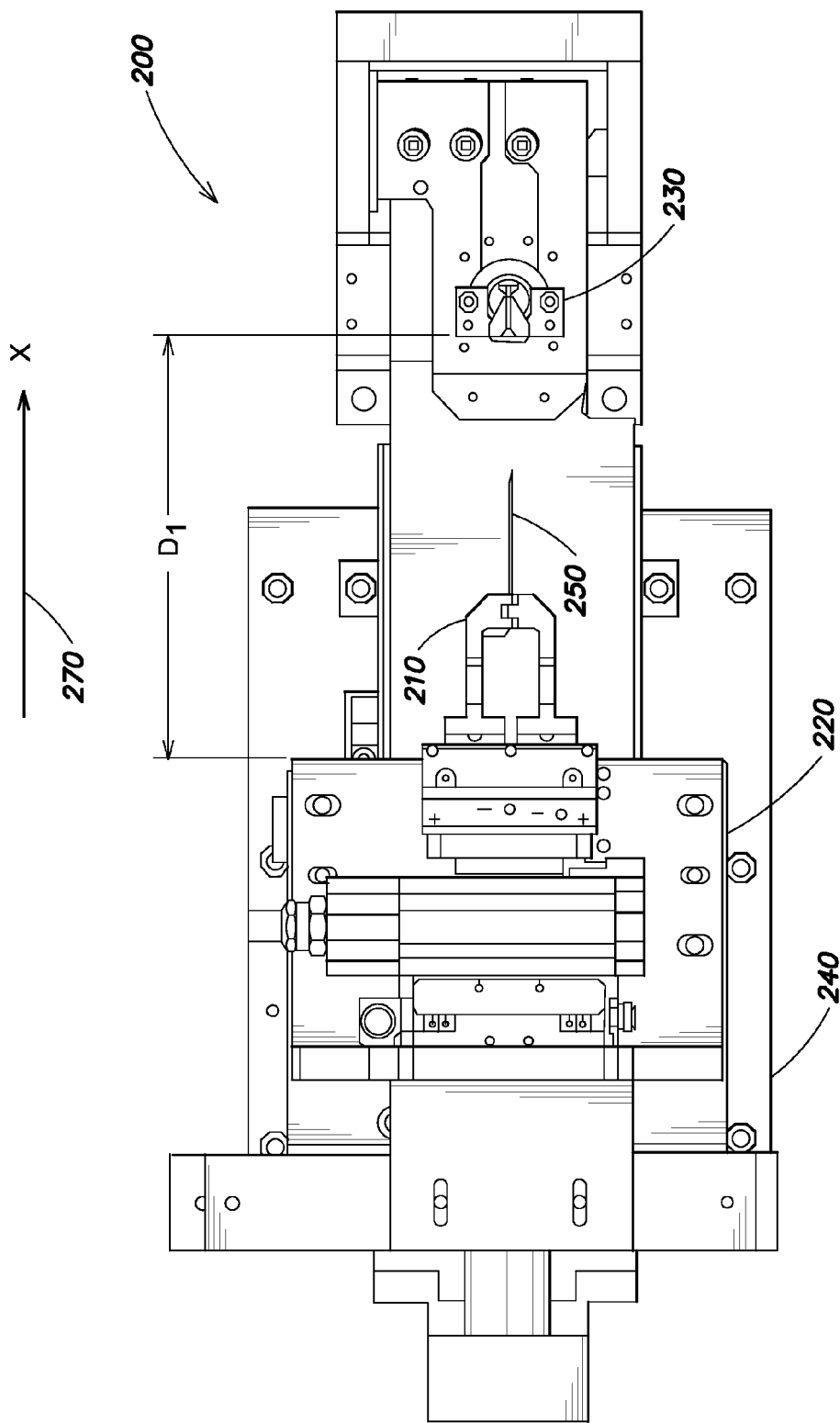
FIGS. 2C-2E are top plan views of the needle bending apparatus of FIG. 2A.
Figure 2D:
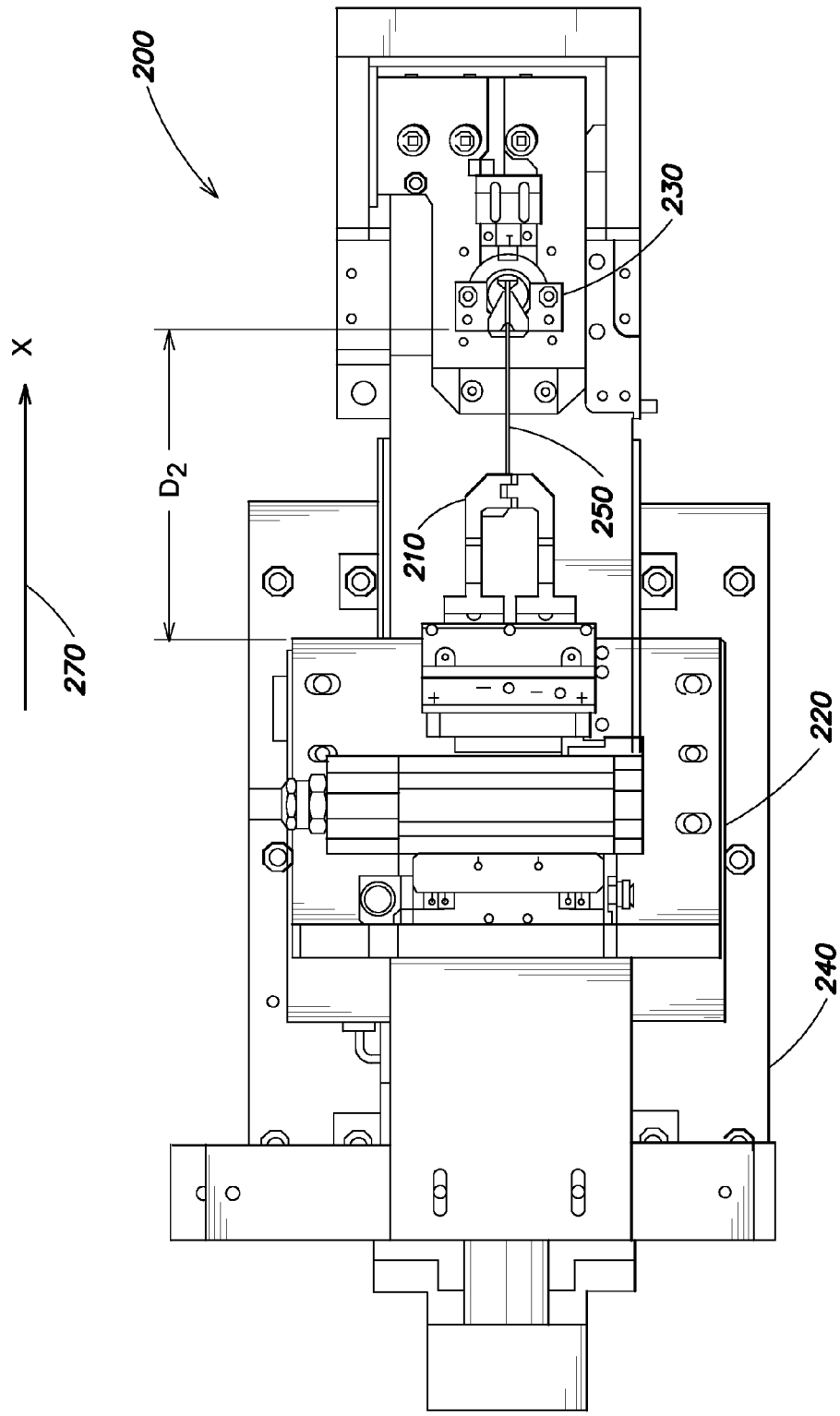
Figure 2E:
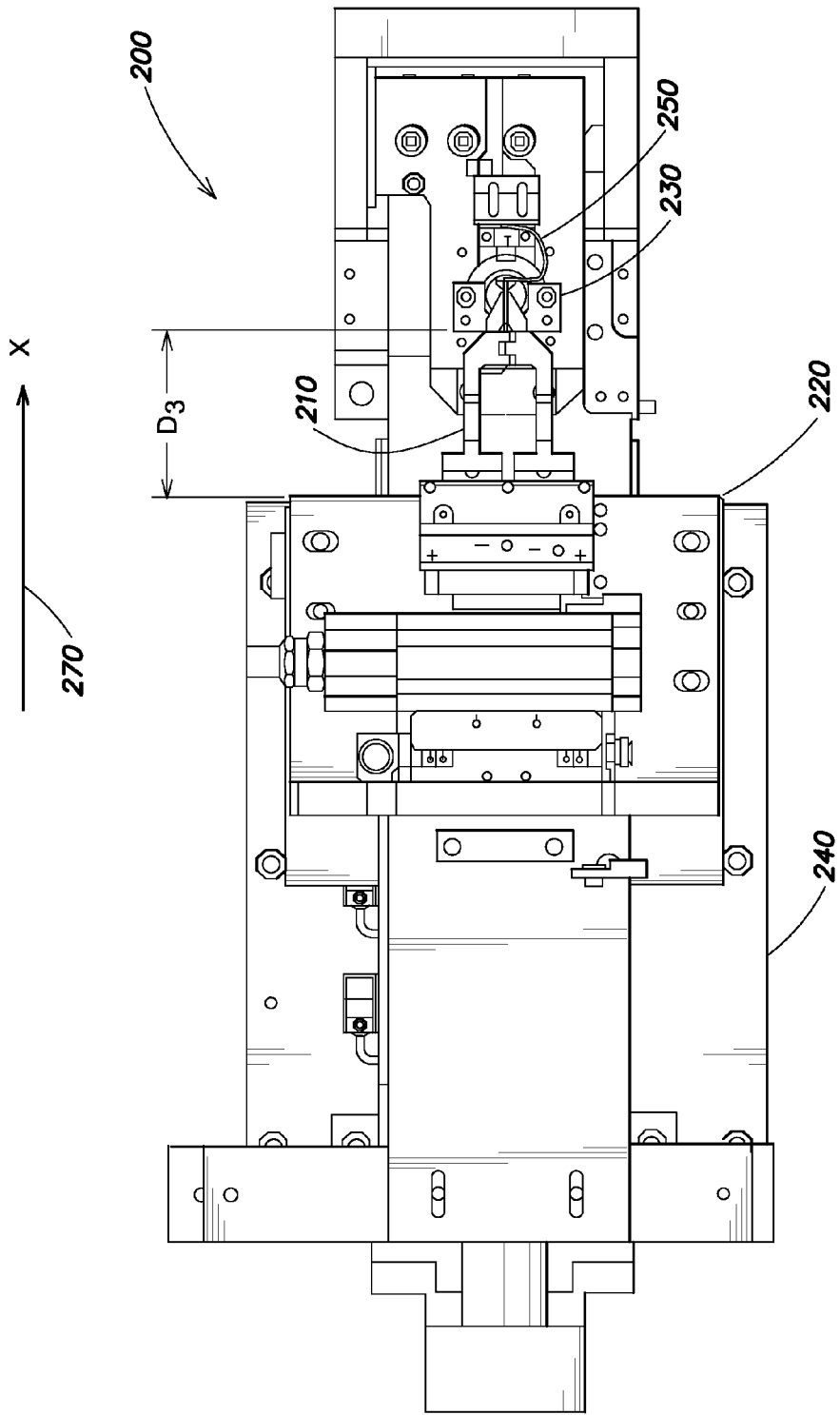

FIG. 2B is a side view of the apparatus 200. FIGS. 2C-E are top plan views of the apparatus 200 showing several exemplary positions of the servo-actuated slide 220 and the needle gripper 210 as the servo-actuated slide 220 moves toward the needle bender 230 along an axis x, indicated at 270. For example, in FIG. 2C, the servo-actuated slide 220 and the needle gripper 210 are positioned at a first distance $D_1$ from the needle bender 230; in FIG. 2D, distance $D_2$ is less than $D_1$; and in FIG. 2E, distance $D_3$ is less than $D_2$. The servo-actuated slide 220 is configured to move in both directions along the x axis 270 for moving the needle gripper 210 towards or away from the needle bender 230.

Figure 3A:
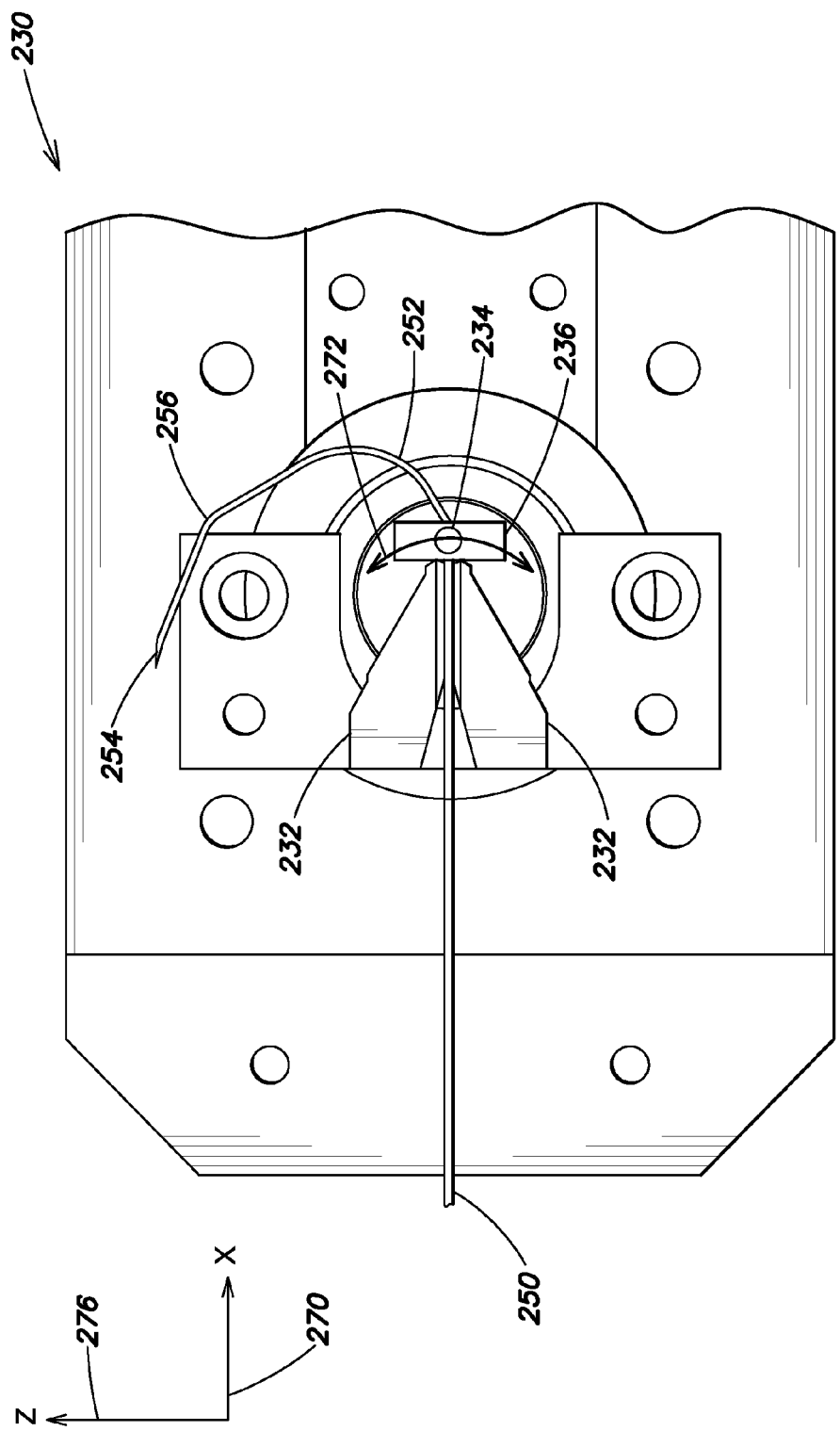
FIG. 3A is a detailed top plan view of a needle bender in accordance with one embodiment.
Figure 3B:
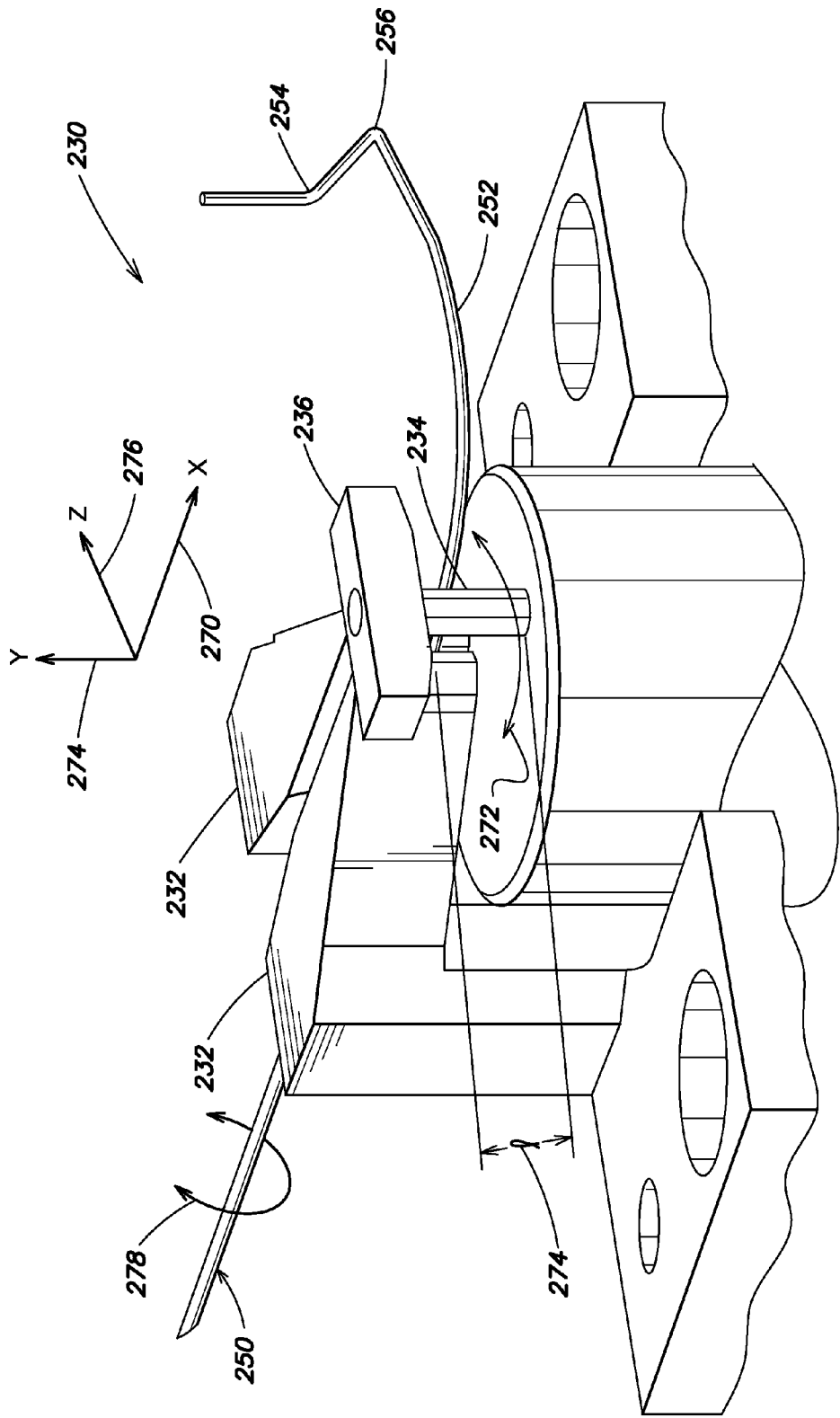
FIGS. 3B and 3C are different perspective views of the needle bender of FIG. 3A.
Figure 3C:
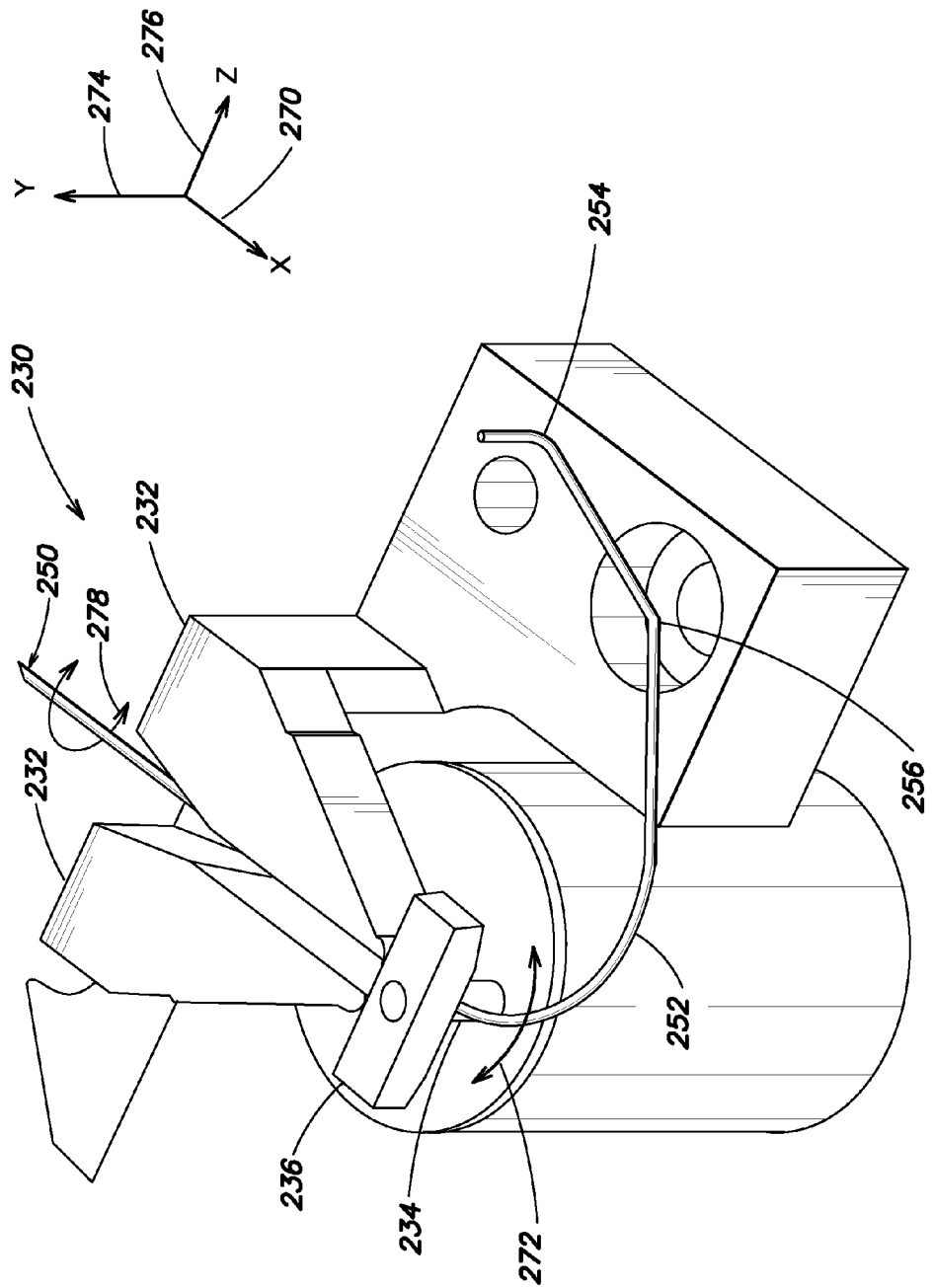
Figure 3D:
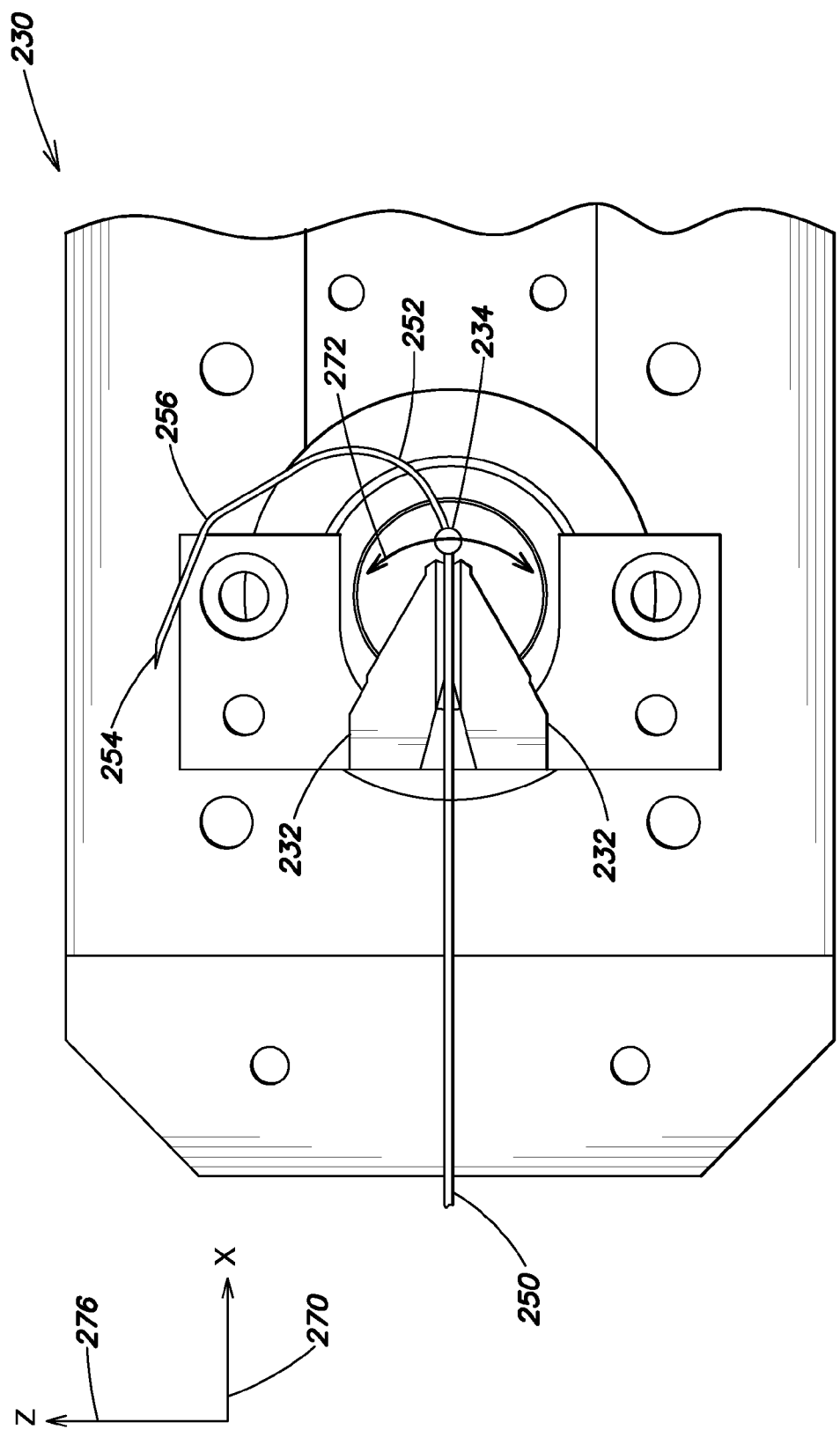
FIG. 3D is a detailed top plan view of a needle bender in accordance with one embodiment.
Figure 3E:
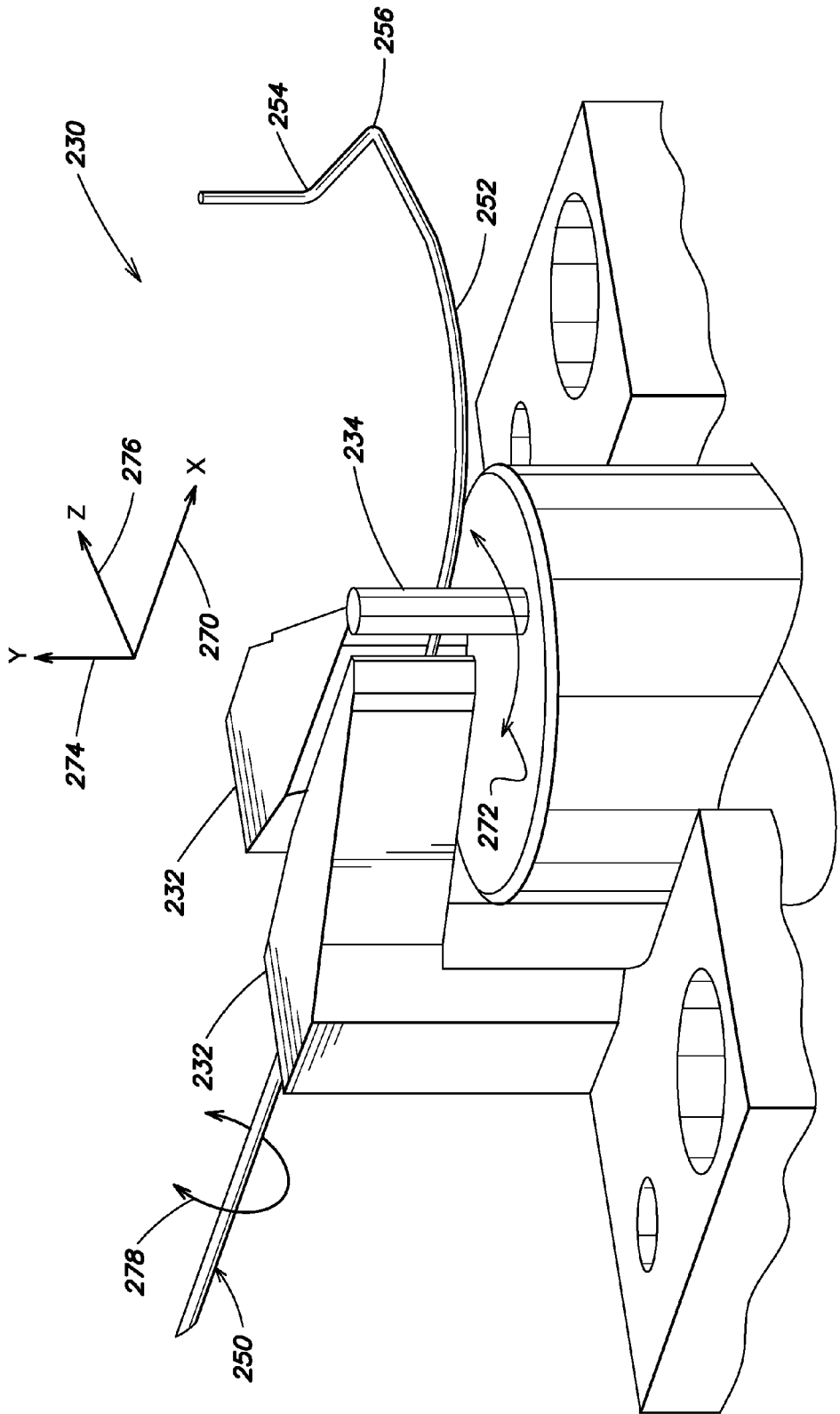
FIGS. 3E and 3F are different perspective views of the needle bender of FIG. 3D.
Figure 3F:
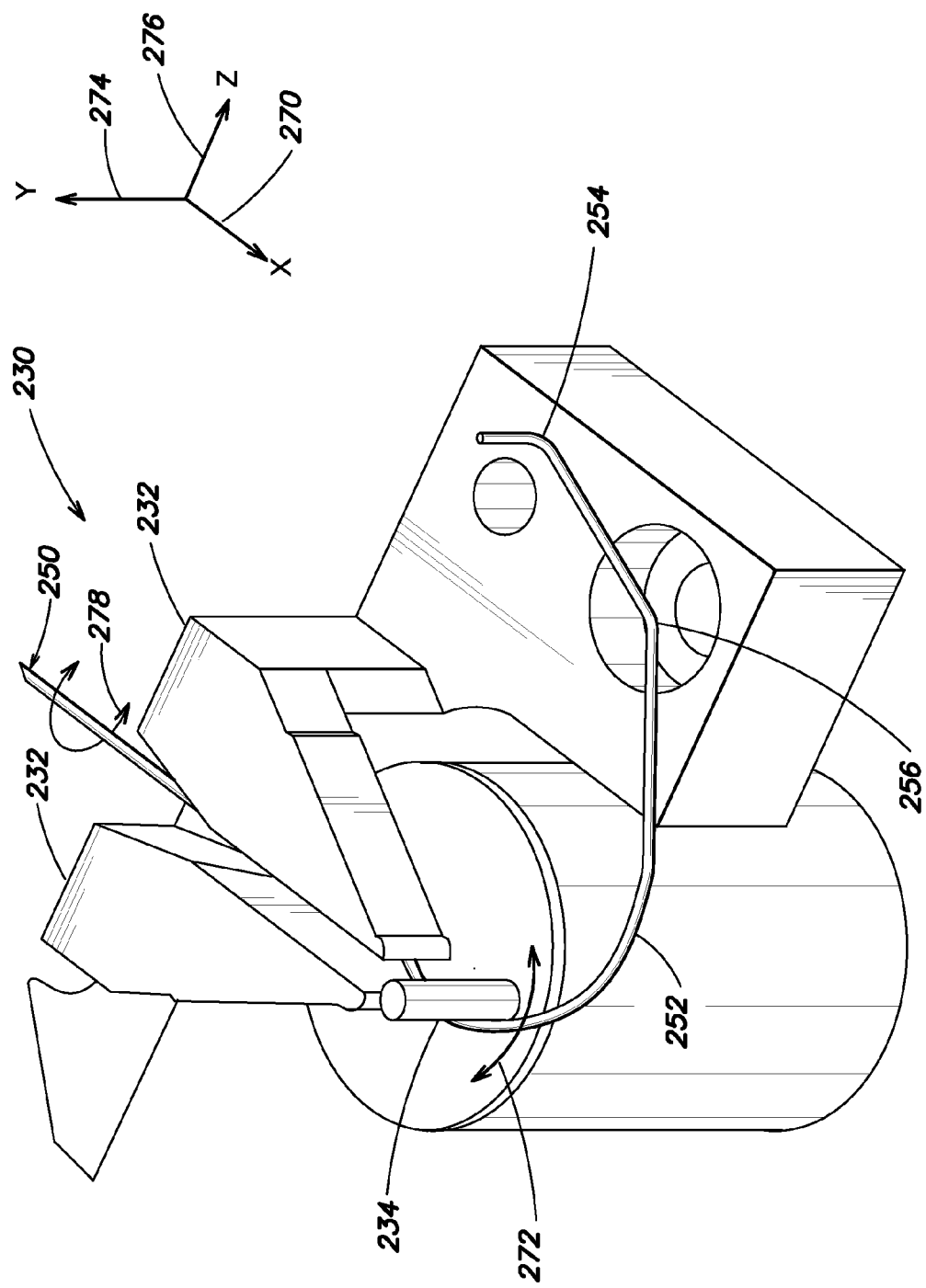

FIG. 3A is a detailed top plan view of the needle bender 230 of FIGS. 2A-C, according to one embodiment, and FIGS. 3B and 3C are different perspective views of the needle bender 230. The needle bender 230 includes one or more bending die 232 and a servo- (or pneumatically-) actuated bending pin 234. In this embodiment, the needle bender 230 further includes a needle restraining member 236 coupled to the bending pin 234; however, in another embodiment, the needle restraining member 236 can be omitted, such as depicted in FIGS. 3D, 3E and 3F. The needle restraining member 236 is positioned adjacent to the needle 250.

When grasping a needle 250, the needle gripper 210 (not shown in FIGS. 3A-C) and the servo-actuated slide 220 (also not shown) are operable to translate the needle 250 along the x axis 270 and adjacent to the bending die 232 to a predetermined bending position (e.g., as determined by a controller). In one example, the needle 250 may pass through a gap between each bending die 232 and adjacent to the bending pin 234. After the needle 250 reaches the predetermined bending position, the bending pin 234 rotates about the bending die 232 in one of the directions shown by arrow 272, which presses a portion of the needle 250 against the bending die 210, thus forming a bend in the needle. The angle of the bend in the needle 250 is a function of the distance the bending pin 234 rotates and the direction of rotation. For example, a small rotational motion of the bending pin 234 may form a bend with a small angle with respect to the x axis 270, while a larger rotational motion of the bending pin 234 may form a bend with a large angle with respect to the x axis 270.

In one embodiment, the needle 250 may have a tendency to ride up along the bending pin 234 as the needle 250 is pressed against the bending die 232 (e.g., the needle 250 may move along an axial length l 274 of the bending pin 234, as indicated in FIG. 3B). The needle restraining member 236 mechanically limits such upward movement of the needle 250 as the bending pin 234 rotates and presses the needle 250 against the bending die 232, thereby preventing undesirable out-of-plane movement of the needle during bending.

After forming the bend, the bending pin 234 retracts or rotates in the opposite direction to move away from the bent portion of the needle 252. The needle gripper 210 and servo-actuated slide 220 may then advance the needle along the x axis 270 to a second predetermined bending position (e.g., as determined by the controller). Additional bends in the needle 250 can be formed by rotating the bending pin 234 such as described above to press against different portions of the needle 250 after the needle is advanced. Bends may be formed by rotating the bending pin 234 in clockwise and/or counter-clockwise directions.

In another embodiment, the needle gripper 210 can rotate the needle 250 about the x axis 270, such as indicated by arrow 278 in FIGS. 3B-C. In this manner, the direction of the bending can be varied. For example, after a first bend 254 in the needle 250 is formed, the needle gripper 210 may rotate the needle 250 prior to forming a second bend 256, such that the first and second bends are formed in different directions (i.e., the bent portions of the needle 250 are along the y and/or z axes 274, 276 with respect to the x axis 270).

Figure 4:
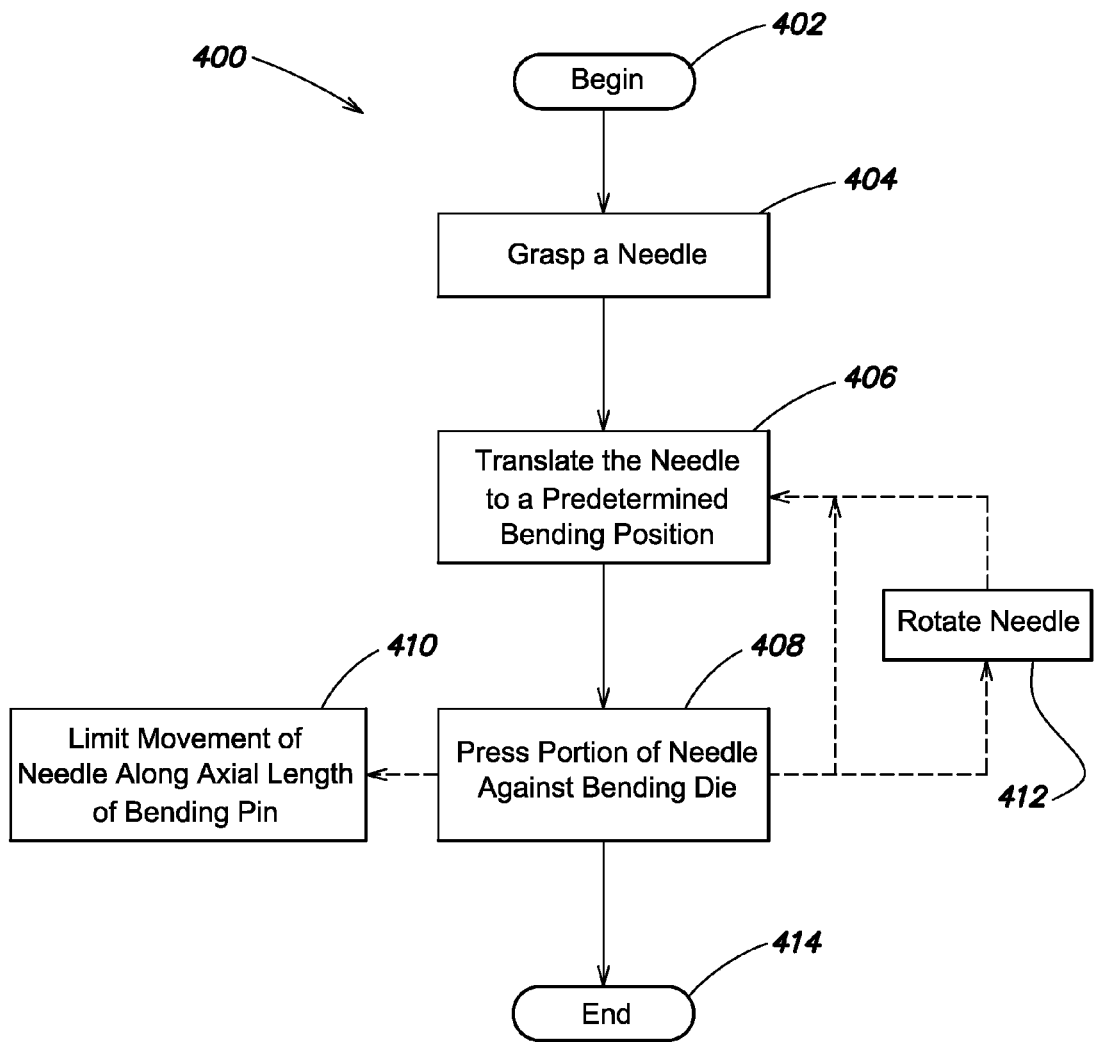
FIG. 4 is a flow diagram of one example of a method of bending a needle in accordance with one embodiment.

FIG. 4 is a flow diagram of one example of a method 400 of bending a needle, in accordance with one embodiment. The method 400 begins at step 402. At step 404, a needle is grasped using a rotatable needle gripper, such as needle gripper 210 in FIGS. 2A-E. At step 406, the needle gripper is translated along a linear path to position the needle at a predetermined bending position with respect to a bending die using a servo-actuated slide, such as servo-actuated slide 220 in FIGS. 2A-E, which is operatively coupled to the needle gripper. The predetermined bending position is a position of the servo-actuated slide along the linear path at which a portion of the needle to be bent is adjacent to a bending die, such as bending die 232 in FIGS. 3A-C. At step 408, a portion of the needle is pressed against the bending die using a servo- (or pneumatically-) actuated bending pin, such as bending pin 234 in FIGS. 3A-C, by rotating the bending pin about a bending axis passing through the linear path (e.g., an axis incident to the needle).

In one embodiment, at step 410, the movement of the needle along an axial length of the bending pin (e.g., a drifting up or down movement of the needle along the bending pin) is mechanically limited by a needle restraining member, such as needle restraining member 236 in FIGS. 3A-C, while the needle is being pressed against the bending die in step 408. In another embodiment, instead of using the needle restraining member, movement of the needle along the axial length of the bending pin can be limited or prevented by making slight rotational adjustments to the pin using a servo rotate of the needle gripper 210. Such rotational adjustments may, for example, be programmably selectable to compensate for any undesirable drifting movement of the needle during bending.

In one embodiment, method 400 ends at step 414 after step 408, for example, when only a single bend is to be formed in the needle. In another embodiment, multiple bends may be formed by repeating steps 406, 408 and 410 as many times as needed. For example, after the first bend is formed, the needle gripper translates the needle forward to a second predetermined bending position, and another portion of the needle is pressed against the bending die to form a second bend. In yet another embodiment, the needle gripper rotates the needle at step 412 between bends so that the next bend is formed in a different direction than the prior bend. In other words, if the needle is not rotated between bends, the next bend will be formed in the same plane or direction as the prior bend. In this manner, multiple bends can be formed in the needle to create a compound bend of a desired radius.

Having thus described several exemplary embodiments of the invention, it is to be appreciated various alterations, modifications, and improvements will readily occur to those skilled in the art. For example, in one embodiment, each needle bending module 260 may be capable of fabricating a bent needle about every eight seconds. In another embodiment, the apparatus 200 may include multiple needle bending modules attached to the frame 240 (e.g., up to six needle bending modules). Such alterations, modifications, and improvements are intended to be part of this disclosure, and are intended to be within the scope of the invention. Accordingly, the foregoing description and drawings are by way of example only.

What is claimed is:

1. An apparatus for bending a hypodermic needle, the apparatus comprising:
    a bending die;
    a needle gripper configured to grasp the hypodermic needle, wherein the needle gripper includes a servo-actuated rotating device configured to rotate the hypodermic needle, via the needle gripper, with respect to the bending die;
    a servo-actuated slide operatively coupled to the needle gripper and configured to translate the needle gripper along a linear path adjacent to the bending die for positioning the hypodermic needle at a predetermined bending position with respect to the bending die; and
    a servo- or pneumatically-actuated bending pin rotatable about a bending axis passing through the linear path, the bending pin being configured to press a portion of the hypodermic needle against the bending die as the bending pin rotates to form a bend in the hypodermic needle;
    wherein the hypodermic needle has a bevel at a first end thereof and a second end opposite the first end, and wherein the apparatus further comprises a machine vision device configured to at least one of:
        determine whether the bevel is correctly oriented with respect to the needle gripper;
        determine a first needle position along the linear path corresponding to the first end of the hypodermic needle; and
        determine a second needle position along the linear path corresponding to the second end of the hypodermic needle.

2. The apparatus of claim 1, further comprising a pick-and-place device configured to place the hypodermic needle into the needle gripper.

3. The apparatus of claim 2, further comprising a bevel orienting device configured to orient the bevel with respect to the needle gripper.

4. The apparatus of claim 3, further comprising:
a hopper configured to contain the hypodermic needle; and
a needle singulator configured to move the hypodermic needle between the hopper and the bevel orienting device.

5. The apparatus of claim 4, further comprising a programmable controller operatively coupled to at least one of the needle gripper, the servo-actuated slide, the bending pin, the machine vision device, the pick-and-place device and the needle singulator, the controller being programmatically configured to:
cause the needle singulator to move the hypodermic needle between the hopper and the bevel orienting device;
cause the pick-and-place device to place the hypodermic needle into the needle gripper;
cause the needle gripper to grasp the hypodermic needle;
cause the servo-actuated rotating device to rotate the hypodermic needle, via the needle gripper, with respect to the bending die to adjust for movement of the hypodermic needle along an axial length of the bending pin as the bending pin rotates or to create a three-dimensional bend in the hypodermic needle;
cause the servo-actuated slide to translate the needle gripper along the linear path to position the hypodermic needle at the predetermined bending position based on at least one of the first needle position and the second needle position; and
cause the bending pin to press the portion of the hypodermic needle against the bending die for forming a bend in the hypodermic needle.

6. The apparatus of claim 5, wherein the predetermined bending position is a first predetermined bending position, wherein the portion of the hypodermic needle is a first portion of the hypodermic needle, wherein the bend in the hypodermic needle is a first bend in the hypodermic needle, and wherein the controller is further programmatically configured to:
cause the servo-actuated slide to translate the needle gripper along the linear path to position the hypodermic needle at a second predetermined bending position; and
cause the bending pin to press a second portion of the hypodermic needle against the bending die to form a second bend in the hypodermic needle.

7. The apparatus of claim 6, wherein the controller is further programmatically configured to cause the needle gripper to rotate through a predetermined angle prior to or while causing the bending pin to press the second portion of the hypodermic needle against the bending die.

8. The apparatus of claim 5, further comprising a user interface operatively coupled to the controller and configured to receive commands from a user representing a position along a length of the hypodermic needle, a bending direction and a bending angle for each bend to be formed in the hypodermic needle, wherein the controller is further configured to receive the commands and to cause the apparatus to form each bend in the hypodermic needle according to the commands.

9. A method of bending a hypodermic needle, the method comprising:
grasping the hypodermic needle using a rotatable needle gripper;
translating the rotatable needle gripper along a linear path to position the hypodermic needle at a predetermined bending position with respect to a bending die using a servo-actuated slide operatively coupled to the needle gripper; and
pressing a portion of the hypodermic needle against the bending die using a servo- or pneumatically-actuated rotating bending pin to form a bend in the hypodermic needle by rotating the bending pin about a bending axis passing through the linear path.

10. The method of claim 9, wherein the hypodermic needle has a bevel at a first end thereof and a second end opposite the first end, and wherein the method further comprises at least one of:
determining whether the bevel is correctly oriented with respect to the rotatable needle gripper using a machine vision device;
determining a first needle position along the linear path corresponding to the first end of the hypodermic needle using the machine vision device; and
determining a second needle position along the linear path corresponding to the second end of the hypodermic needle using the machine vision device.

11. The method of claim 10, wherein translating the rotatable needle gripper along the linear path to position the hypodermic needle at the predetermined bending position is performed based on at least one of the first needle position and the second needle position.

12. The method of claim 11, wherein the predetermined bending position is a first predetermined bending position, wherein the portion of the hypodermic needle is a first portion of the hypodermic needle, wherein the bend in the hypodermic needle is a first bend in the hypodermic needle, and wherein the method further comprises:
translating the rotatable needle gripper along the linear path to position the hypodermic needle at a second predetermined bending position using the servo-actuated slide.

13. The method of claim 12, further comprising rotating the rotatable needle gripper through a predetermined angle about the linear path using a servo-actuated rotating device prior to pressing the second portion of the hypodermic needle against the bending die.

14. The method of claim 13, further comprising pressing a second portion of the hypodermic needle against the bending die to form a second bend in the hypodermic needle using the bending pin such that the hypodermic needle is bent in three dimensions.

* * * * *